United States Patent [19]

Ronsen et al.

[11] Patent Number: 5,010,058

[45] Date of Patent: Apr. 23, 1991

[54] 3,5,6-SUBSTITUTED DERIVATIVES OF 1,2-O-ISOPROPYLIDENE-α,D-GLUCOFURANOSE AND INTERMEDIATES FOR PREPARING THESE DERIVATIVES

[75] Inventors: Bruce Ronsen, River Forest; Sudershan K. Arora, Westchester; Albert V. Thomas, Niles, all of Ill.

[73] Assignee: 501 Greenwich Pharmaceuticals Incorporated, Ft. Washington, Pa.

[21] Appl. No.: 369,932

[22] Filed: Jun. 22, 1989

[51] Int. Cl.$^5$ .............................................. A61K 31/70
[52] U.S. Cl. ........................................ 514/23; 514/25; 514/825; 514/861; 536/1.1; 536/4.1; 536/17.2; 536/17.5; 536/18.7; 536/54
[58] Field of Search ................... 514/23, 25, 825, 861; 536/1.1, 4.1, 17.2, 17.5, 18.7, 54

[56] References Cited

U.S. PATENT DOCUMENTS

| | | | |
|---|---|---|---|
| Re. 30,354 | 7/1980 | Gordon | 536/4.1 |
| Re. 30,379 | 8/1980 | Gordon | 536/4.1 |
| Re. 32,268 | 10/1986 | Gordon | 514/25 |
| 2,461,478 | 2/1890 | Kaszuba | 106/135 |
| 2,875,194 | 2/1959 | Baker et al. | 536/17.3 |
| 2,960,452 | 11/1960 | Slager et al. | 549/361 |
| 3,586,664 | 6/1971 | Kohno et al. | 536/4.1 |
| 3,832,355 | 8/1974 | Jaffe et al. | 549/361 |
| 3,939,145 | 2/1976 | Gordon | 536/17.9 |
| 3,939,146 | 2/1976 | Gordon | 514/25 |
| 3,965,262 | 6/1976 | Gordon | 514/53 |
| 4,010,275 | 3/1977 | Wilhelmi | 514/23 |
| 4,016,261 | 4/1977 | Gordon | 536/120 |
| 4,017,608 | 4/1977 | Gordon | 536/120 |
| 4,032,650 | 6/1977 | Molle et al. | 514/470 |
| 4,056,322 | 11/1977 | Gordon | 536/4.1 |
| 4,220,782 | 9/1980 | Stoltefuss | 536/4.1 |
| 4,251,520 | 2/1981 | Bruzzese et al. | 536/4.1 |
| 4,554,349 | 11/1985 | Ponpipom et al. | 536/55 |
| 4,735,934 | 4/1988 | Gordon | 514/825 |
| 4,738,953 | 4/1988 | Gordon | 514/25 |

Primary Examiner—Ronald W. Griffin
Attorney, Agent, or Firm—Finnegan, Henderson, Farabow, Garrett & Dunner

[57] ABSTRACT

Derivatives of 1,2-O-isopropylidene-α,D-glucofuranose and intermediates for preparing these derivatives are described. These derivatives are useful for treating animals and mammals with inflammatory and/or autoimmune disorders such as autoimmune deficiency syndrome, psoriasis, atopic dermatitis, rheumatoid arthritis, osteoarthritis, scleroderma and systemic lupus erythematosus.

104 Claims, No Drawings

3,5,6-SUBSTITUTED DERIVATIVES OF 1,2-O-ISOPROPYLIDENE-α,D-GLUCOFURANOSE AND INTERMEDIATES FOR PREPARING THESE DERIVATIVES

BACKGROUND OF THE INVENTION

1. Field of the Invention

This invention relates to 3,5,6-substituted derivatives of 1,2-O-isopropylidene-α,D-glucofuranose compounds and intermediates for preparing these derivatives. More particularly, this invention relates to derivatives of 1,2:3,5-Di-O- and 1,2:5,6-Di-O-isopropylidene-6-deoxy-α,D-glucofuranose. It also relates to furanosides obtained when 1,2-O-isopropylidene residues are reacted with methanol or other aliphatic alcohols of up to seven carbon atoms, both branching and containing double bonds. It further encompasses glucofuranose and related hexofuranose compounds wherein chirality is changed at positions 3 and 5. The derivatives of this invention have anti-proliferation and anti-inflammatory activity and are useful for treating animals and mammals with inflammatory and/or autoimmune disorders such as autoimmune deficiency syndrome, psoriasis, atopic dermatitis, rheumatoid arthritis, osteoarthritis, scleroderma and systemic lupus erythematosus.

2. Description of the Related Art

Blocked acetals of hexoses exist as solids or liquids at room temperature. Various blocking methods are described in U.S. Pat. Nos. 2,715,121 and 4,056,322, the disclosures of which are incorporated by reference herein in their entireties. For example, in instances where an aldehyde or ketone is reacted with the hydroxyl groups on adjacent or neighboring sugar carbon atoms, the hexose may be blocked in a plurality of positions, such as, e.g., the 1,2- and/or 5,6- positions. In the 1,2:5,6-blocked hexoses the ring forms between carbons 1 and 4, leaving carbon 3 free to etherize and in the 1,2:3,5-blocked hexoses, the ring forms between carbons 1 and 4, leaving carbon 6 free to etherize. Thus, 1,2:5,6-blocked hexoses may form 3-O ethers, and 1,2:3,5-blocked hexoses may form 6-O ethers. After the desired blocking of the monosaccharide is obtained, the unblocked position of the monosaccharide can be etherized.

The 3- and 6-substituted furanoses thus obtained are generally known to have anti-inflammatory activity. Specific therapeutic compounds such as amiprilose hydrochloride, 1,2-O-Isopropylidene-3-O-3('N,N'-dimethylamino-n-propyl)-α,D-glucofuranose (i.e. THERAFECTIN®), have been known for some time. This compound has demonstrated utility in managing the signs and symptoms of rheumatoid arthritis while exhibiting little toxicity. It is generally known that furanose compounds have activity as immuno-moduiators, and therefore, may have a therapeutic effect on other autoimmune disorders such as psoriasis, eczema or lupus. For certain of these indications, high doses of these monosaccharides, such as THERAFECTIN®, are needed to produce effective results. Consequently, they are difficult to prescribe orally. As therapy for those conditions is often midterm or longterm, there is a need to develop potent, non-toxic compounds which can be orally administered to promote patient compliance.

It is therefore an object of the present invention to provide substituted 1,2-O-isopropylidene-α,D-glucofuranose compounds that exhibit significantly greater potency than available compounds, such as THERAFECTIN®, in order to provide ease of oral administration. It is believed that the compounds of the present invention act by a different mechanism than THERAFECTIN® and are more selective in their activity.

Additional objects and advantages of the invention will be set forth in the description which follows, and in part will be apparent from the description, or may be learned by practice of the invention. The objects and advantages of the invention may be realized and obtained by means of the mechanisms and combinations pointed out in the appended claims.

SUMMARY OF THE INVENTION

To achieve the foregoing objects, and in accordance with the purposes of the invention as embodied and broadly described herein, there is provided a monosaccharide compound of formula I:

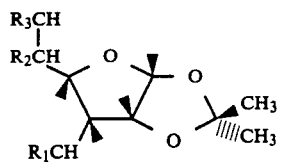

wherein $R_1$ is a member selected from the group consisting of hydrogen, an alkoxy radical containing from 4 to 11 carbon atoms, a hydroxyl residue, an aralkyl radical containing at least 7 carbon atoms, and a radical of the formula

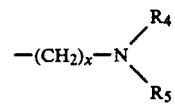

in which x is a whole number up to 7 and $R_4$ and $R_5$ are each H, OH, or alkoxy radical of up to 7 carbons.

$R_2$ is a member selected from the group consisting of hydrogen, an alkoxy radical containing from 4 to 7 carbon atoms, a methyl thio carbonyl, and a radical of the formula

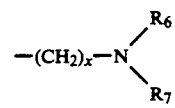

in which x is a whole number up to 7 and $R_6$ and $R_7$ are each H, OH, or alkoxy radical of up to 7 carbons;

$R_1$ and $R_2$ together can form an isopropylidene radical;

$R_3$ is a member selected from the group consisting of hydrogen, a halogen, an alkylene radical, an aralkyl radical containing at least 7 carbon atoms, a radical of the formula

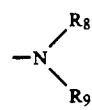

in which $R_8$ is hydrogen and $R_9$ is an alkyl radical containing up to eleven carbon atoms and a radical of the formula

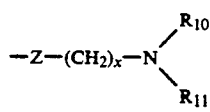

in which Z is thio or amino, x is a whole number up to 7 and $R_{10}$ and $R_{11}$ are each H, OH or an alkoxy radical of up to 7 carbons; and $R_2$ and $R_3$ together can form an isopropylidene radical.

As used herein, the term "alkyl" comprehends both straight and branched hydrocarbon groups containing from 1 to 11 carbon atoms, such as methyl, ethyl, propyl, isopropyl, etc. The hydroxy-lower alkyl groups have a hydroxy group on an alkyl chain like those described above, preferably on the terminal carbon, e.g., 2-hydroxyethyl, etc. The term "aralkyl" includes phenyl lower alkyl radicals containing from 7 to 13 carbon atoms, such as benzyl, phenethyl, phenpropyl, etc. The terms alkoxy and aralkoxy denote alkyl and aralkyl groups as defined above containing oxygen. The term "aryl" denotes phenyl and substituted phenyl groups such as lower alkyl phenyl and lower alkoxy phenyl including methyl phenyl, ethyl phenyl, ethoxy phenyl, and methoxy phenyl. The term "lower alkylene" includes both straight and branched chain alkylene radicals containing from 2 to 7 carbon atoms such as ethylene, propylene, butylene, etc.

Specific embodiments of this formula include 1,2:3,5-Di-O-isopropylidene-6-deoxy-6-amino-heptyl-α,D-glucofuranose;

1,2-O-isopropylidene-6-deoxy-6-aminoundecyl-α,D-glucofuranose;

1,2-O-isopropylidene-3-O-(n-heptyl)-6-deoxy-α,D-glucofuranose;

1,2-O-isopropylidene-3-O-(n-heptyl)-6-deoxy-6-aminoheptyl-α,D-glucofuranose;

1,2-O-isopropylidene-5-O-n-heptyl-6-deoxy-α,D-glucofuranose:

1,2-O-isopropylidene-3-O-3'-(N'-N'-dimethylaminopropyl)-5-O-n-heptyl-6-deoxy-α,D-glucofuranose.

1,2-O-isopropylidene-6-deoxy-6-N-3'-(N',N'-dimethylamino-n-propyl)-α,D-glucofuranose;

1,2-O-isopropylidene-3-O-heptyl-6-deoxy-6-S-heptyl-α,D-glucofuranose;

1,2-O-isopropylidene-5-deoxy-3-O-heptyl-α,D-glucofuranose;

1,2-O-isopropylidene-3-deoxy-5,6-O[3'-di-(N',N'-dimethylamino-n-propyl)]-α,D-glucofuranose;

1,2-O-isopropylidene-3,6-dideoxy-6-N-3'-(N',N'-dimethylamino-n-propyl)-α,D-glucofuranose;

1,2-O-isopropylidene-6-deoxy-6-S-3'-(N',N'-dimethylamino-n-propyl)-α,D-glucofuranose.

1,2:5,6-Di-O-isopropylidene-3-deoxy-3-C-ethyl-2'-N-3'-(N'-propylimidozalyl)-α,D-allofuranose; and Methyl 2-O-heptyl-D-glucofuranoside.

The present invention also provides a pharmaceutical composition for the treatment of inflammatory and/or autoimmune disorders. The composition comprises an effective amount of at least one of these monosaccharide compounds or a physiologically acceptable acid-addition salt thereof with a pharmaceutically acceptable carrier.

These compounds have demonstrated decreased skin cell proliferation and inhibition of the proliferative response of splenic T-lymphocytes to known mitogens in in vitro tests. T-lymphocytes are the immune cells that regulate immune responses. Therefore, it is believed that the present monosaccharides can be used for treating animals and humans with inflammatory and/or autoimmune disorders such as autoimmune deficiency syndrome, psoriasis, atopic dermatitis, rheumatoid arthritis, ostearthritis, scleroderma and systemic lupus erythematosus.

Advantageously, the compounds of the present invention exhibit greater potency in terms of their activity than known monosaccharides such as THERAFECTIN ®. Therefore, the present compounds can be administered internally as well as externally.

DETAILED DESCRIPTION OF THE INVENTION

The compounds of the present invention include the following monosaccharides identified by name and number:

1,2:3,5-Di-O-isopropylidene-6-deoxy-6-amino-heptyl-α,D-glucofuranose (Empirical formula $C_{19}H_{35}N_1O_5$) having the following structural formula;

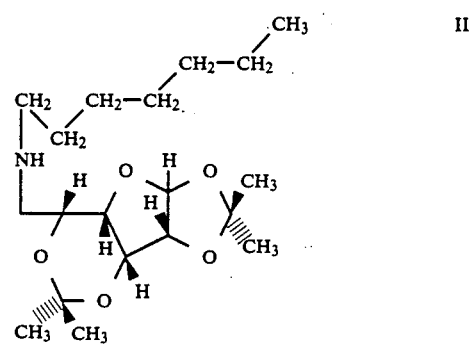

1,2-O-isopropylidene-6-deoxy-6-aminoundecyl-α,D-glucofuranose (Empirical formula $C_{20}H_{39}N_1O_5$) having the following structural formula;

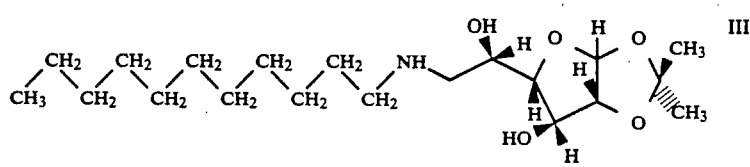

1,2-O-isopropylidene-3-O-(n-heptyl)-6-deoxy α,D-glucofuranose (Empirical formula $C_{16}H_{30}O_5$) having the following structural formula;

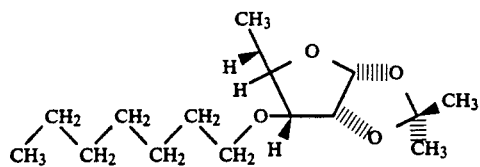

1,2-O-isopropylidene-3-O-(n-heptyl)-6-deoxy-6-aminoheptyl-α,D-glucofuranose (Empirical formula $C_{23}H_{45}N_1O_5$) having the following structural formula;

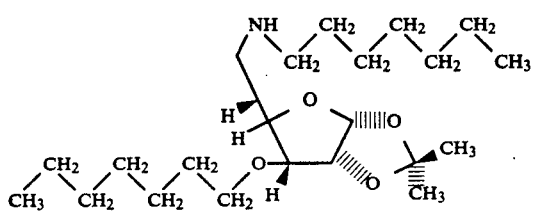

1,2-O-isopropylidene-6-deoxy-5-O-n-heptyl-α, D-glucofuranose (Empirical formula $C_{16}H_{30}O_5$) having the following structural formula; and

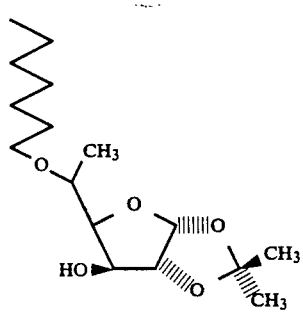

1,2-O-isopropylidene-6-deoxy-3-O-3'-(N'-N'-dimethylaminopropyl)-5-O-N-heptyl-α, D-glucofuranose (Empirical formula $C_{21}H_{41}N_1O_5$) having the following structural formula;

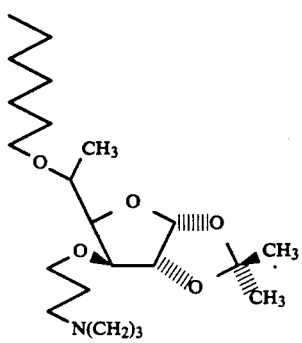

1,2-O-isopropylidene-6-deoxy-6-N-3'-(N',N'-dimethylamino-n-propyl)-α, D-glucofuranose (Empirical formula $C_{14}H_{28}N_2O_5$) having the following structural formula;

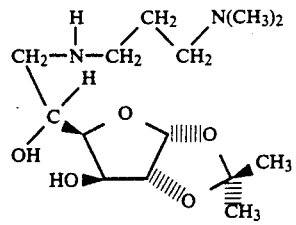

1,2-O-isopropylidene-3-O-heptyl-6-deoxy 6-S-heptyl-α,D-glucofuranose (Empirical formula $C_{23}H_{44}S_1O_5$) having the following structural formula;

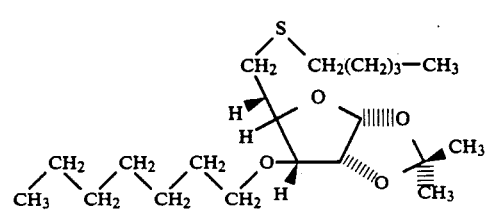

1,2-O-Isopropylidene-5-deoxy-3-O-heptyl-α,D-glucofuranose (Empirical formula $C_{16}H_{30}O_5$) having the following structural formula;

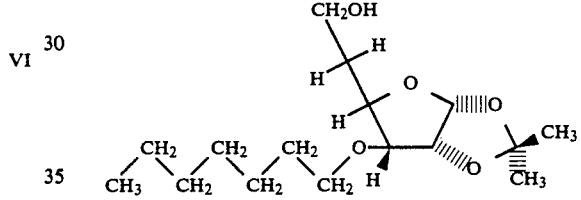

1,2-O-Isopropylidene-3-deoxy-5,6-O[3'-di-(N',N'-dimethylamino-n-propyl)]-α, D-glucofuranose (Empirical formula $C_{19}H_{38}N_2O_5$) having the following structural formula;

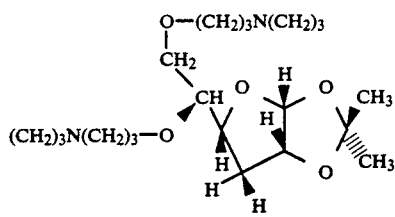

1,2-O-Isopropylidene-3-6 dideoxy-6-N-3'-(N',N'-dimethylamino-n-propyl)-α,D-glucofuranose (Empirical formula $C_{14}H_{27}N_2O_4$) having the following structural formula;

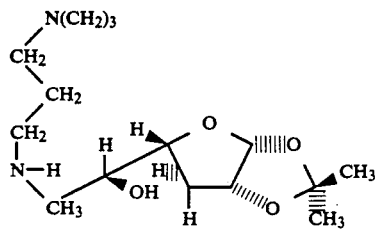

1,2-O-Isopropylidene-6-deoxy-6-S-3'-(N',N'-dimethylamino-n-propyl)-α,D-glucofuranose (Empirical formula $C_{14}H_{27}N_1S_1O_5$) having the following structural formula;

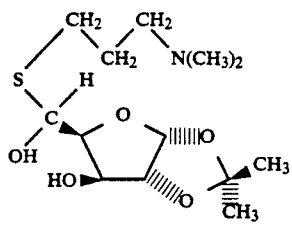

XIII 1,2:5,6-Di-O-Isopropylidene-3-deoxy-3-C-ethyl-2'-N-3'-(N'-propyl imidazolyl)-α,D-allofuranose (Empirical formula $C_{20}H_{33}N_3O_5$) having the following structural formula; and

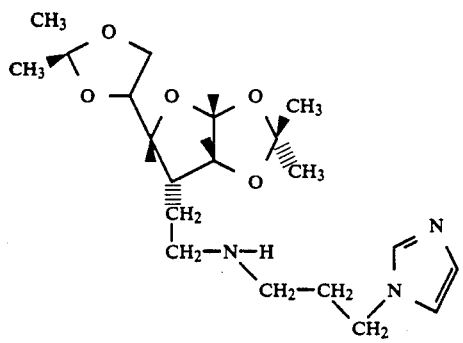

XIV

Methyl 2-O-heptyl-D-glucofuranoside (Empirical formula $C_{14}H_{28}O_6$) having the following structural formula;

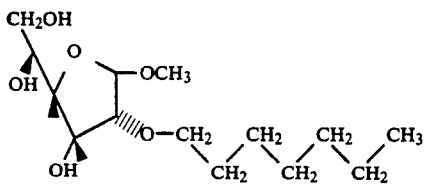

XV

The compounds of the present invention are useful for treating animals and mammals with inflammatory and/or autoimmune disorders such as psoriasis, atopic dermatitis, rheumatoid arthritis, osteoarthritis, scleroderma and systematic lupus erythematosus.

Due to their valuable pharmacological properties, the monosaccharide compounds of the present invention or their physiologically acceptable acid-addition salts are particularly suitable for use as active compounds in pharmaceutical compositions for the treatment of, for example, inflammatory rheumatic disorders. The compounds can either be administered alone in the form of microcapsules, in mixtures with one another or in combination with acceptable pharmaceutical carriers.

The invention thus also relates to pharmaceutical compositions which comprise an effective amount of at least one compound of the present invention, if appropriate, in the form of an acid-addition salt, with or without a pharmaceutically and physiologically acceptable carrier. Also provided is a method of treating animals or humans suffering from inflammatory and/or autoimmune disorders which comprises administering thereto an effective amount of at least one of the compounds of the invention or an acid-addition salt thereof, with or without a pharmaceutically acceptable carrier.

The compositions according to the invention can be administered orally, topically, rectally, internasally, or, if desired, parenterally; oral administration is preferred.

Suitable solid or liquid galenic formulations are, for example, granules, powders, coated tablets, microcapsules, suppositories, syrups, elixers, suspensions, emulsions, drops or injectable solutions, and also preparations having a protracted release of the active compound, in the production of which adjuvants, such as excipients, disintegrants, binders, coating agents, swelling agents, glidants, or lubricants, flavors, sweetners or solubilizers are usually used. Frequently used adjuvants which may be mentioned are, for example, magnesium carbonate, titanium dioxide, lactose, mannitol and other sugars, talc, lactalbumin, gelatin, starch, cellulose and its derivatives, animal and vegetable oils, polyethylene glycols and solvents, such as, for example, sterile water and monohydric or polyhydric alcohols, for example, glycerol.

The pharmaceutical compositions are preferably produced and administered in dosage units, each unit containing as active component a certain dose of at least one compound of the present invention and/or at least one of its physiologically acceptable acid-addition salts. In the case of animals or humans, the dose can range from about 1 to 100 mg per kilogram of body weight per day, preferably 10–100 mg. In the case of in vitro testing, the effective amount to achieve a 50% inhibition of the cultured cells range from about 1–100 mg/ml of culture medium, preferably 10–100 mg/ml.

The following examples are to be considered as illustrative only, and are not to be considered as limitative in any manner of the claims which follow. In these examples, NMR were recorded on a Varian XL-300 MHz using TMS as the internal standard reference, CIMS and high resolution mass spectroscopy were obtained on a Finnegan MAT-90 mass spectrometer, FTIR spectra were recorded on a Perkin-Elmer 1600 instrument using KBr plates and optical rotation was measured on a Perkin-Elmer model 241 polarimeter.

The 1,2:3,5-Di-O-isopropylidene-α,D-glucofuranose ($DGF_1$) used as the basic starting material of the compounds of Examples 1 and 2 was prepared according to Steps 1–3 of Example 1. The simple and efficient process for preparing 1,2:3,5-Di-O-isopropylidene-α,D-glucofuranose has been described in U.S. patent application Ser. No. 07/294,838, which is incorporated herein in its entirety. DGF, 1,2:5,6-Di-O-isopropylidene α, D-glucofuranose, was obtained from Aldrich Chemical Co., Milwaukee, Wis. or made in-house according to the procedures described in U.S. Pat. No. 2,715,121 to Glen et al.

EXAMPLE 1

1,2:3,5-Di-O-isopropylidene-6-deoxy-6-aminoheptyl-α, D-glucofuranose

Step 1

To a stirred solution of 1,2-O-isopropylidene-α,D-glucofuranose (i.e., 220 g, 1.0 mole) in dry $CH_2Cl_2$ (300 ml) was added dry pyridine (300 ml). Trimethylacetyl chloride (120.5 g, 1 mole) was then added dropwise, with stirring at room temperature, over a period of 30 minutes until all the trimethylacetyl chloride had been added. A GC analysis showed the complete disappearance of the starting material. Dichloromethane was removed with rotary evaporation and then subjected to high vacuum to remove pyridine. water (300 ml) was added to the reaction flask and the solid formed was filtered, washed with water and dried. It was then recrystallized from methanol. The yield of the pure product, 1,2-O-isopropylidene-6-O-(trimethylacetyl)-α,D-glucofuranose, was 290 g (95.39%) m.p 151°-151.7° C.

NMR (CDCl$_3$): s 5.99 (d, 1H, H$_1$), 4.58 (d, 1H, H$_2$), 4.44 (m, 1H, H$_4$), 4.39 (m, 1H, H$_3$), 4.25 (m, 2H,H$_6$), 4.10 (m, 1H,H$_5$), 3.13 (d, 1H,OH), 3.06 (d, iH,OH), 1.50 (S, 3H,CH$_3$), 1.34 (s, 3H,CH$_3$), 1.25 (s, 9H,—C(CH$_3$)$_3$

CIMS: 322 (M+18), 626 (Dimer+18).

Step 2

144 g, 0.473 moles of 1,2-O-isopropylidene-6-O-(trimethylacetyl)-α,D-glucofuranose was added to dimethoxypropane (400 ml) and a catalytic amount of p-toluene sulfonic acid (4 g) and refluxed for 30 minutes. (The progress of the reactions was followed by TLC and GC.) After the reaction was complete, the flask was cooled and the excess of dimethoxypropane was removed under rotary evaporator. The residue so formed was dissolved in CH$_2$Cl$_2$ (250 ml), washed with saturated NaHCO$_3$ solution (3×50 ml), and brine (2×25 ml). The organic layer was dried (anhydrous MgSO$_4$) and the solvent removed. The product, 1,2:3,5-Di-O-isopropyli-dene-6-O-(trimethylacetyl)-α,D-
glucofuranose showed a single homogenous spot on TLC and was used as such for the next step without further purification. yield of the colorless oil was 154 g (94.5%).

NMR (CDCl$_3$): s 5.99 (d, 1H), 4.65 (d, 1H), 4.30 (m, 1H), 4.16 (m, 1H), 3.77 (m, 1H), 1.486 (S. 3H), 1.353 (S, 3H), 1.339 (S, 3H), 1.331 (S, 3H), 1.206 (S, 9H).

CIMS: 345 (M+1), 362 (M+18).

Step 3

1,2:3,5-Di-O-isopropylidene-6-O(trimethylacetyl)-α,D-glucofuranose (125 g, 0.366 moles) as obtained in Step 2 was suspended in aqueous sodium hydroxide solution (126 g NaOH dissolved in 500 ml of distilled water) and the mixture refluxed, with ample stirring, for 40 min. (The progress of the reaction was monitored by GC and TLC.) After the completion of the reaction, the reaction mixture was cooled and extracted with dichlorometbane (4×200 ml), washed with cold water (3×50 ml), organic layer dried (MgSO$_4$) and the solvent removed. The colorless viscous oil so formed showed a single homogenous spot on the TLC. Upon standing the compound crystallized to a white solid having a melting point of 96.5° to 97.2° C. The yield of the product, 1,2:3,5-Di-O-isopropylidene-α, D-glucofuranose, hereinafter DGF$_1$, was 95 g (100%).

[a] at 25° : D spectral line of sodium=+51.8° in methanol. IR (neat): 3475 Cm$^{-1}$(broad OH).

NMR (CDCl$_3$): s 6.01 (d. 1H, H$_1$), 4.60 (m, 1H,H$_2$), 4.37 (m, 1H,H$_4$), 4.20 (d, IH,H$_3$), 3.86 (m, 1H,H$_6$), 3.65 (m, 2H, CH$_2$—OH), 1.92 (bs, 1H,OH, D$_2$O exchangeable), 1.50 (s, 3H), 1.37 (S, 6H), 1.34 (S, 3H).

CIMS: 261 (M+1), 278 (M+18).

Step 4

To a stirred solution of DGF$_1$ (26.0 g, 0.1 mole) in anhydrous pyridine (100 ml) was added a solution of p-toluenesulfonyl chloride (20.95 g, 0.109 mole) in anhydrous pyridine (100 ml), dropwise, over a period of 20 minutes at room temperature. After the complete addition of p-toluenesulfonyl chloride solution, the mixture was stirred for another 3 hours (the progress was followed by TLC) at the same temperature. The pyridine was then removed under diminished pressure and the residue extracted with ethylacetate (250 ml), washed with water (1×50 ml), saturated solution of sodium bicarbonate (3×50 ml) and brine (1×100 ml). The ethyl acetate layer was then dried (magnesium sulfate) and the solvent removed. The light yellow solid so formed was recrystallized from etherhexane to yield 1,2:3,5-Di-O-isopropylidene-6-tosyl-α, D-glucofuranose (I), a white crystalline material in 97% yield, mp 72.3°-72.6° Celsius.

CIMS: 432 (M+18)

Step 5

A mixture of 1,2:3,5-di-O-isopropylidene-6-tosyl-α, D-glucofuranose (20.7 g, 0.05 moles) and 1-aminoheptane (14.37 g, 0.125 moles) was heated in an oil bath at 80°-90° C. for 3 hours. The reaction mixture was then cooled, dissolved in ethyl acetate (250 ml), washed with saturated solution of sodium bicarbonate (3×50 ml) and brine (1×50 ml). The ethyl acetate layer was then dried (anhydrous magnesium sulfate) and the solvent removed. The light yellow viscous oil so obtained was purified with flash chromatography usinq 20% ether in hexane. The yield of the pure product, 1,2:3,5-Di-O-isopropylidene-6-deoxy-6-aminoheptyl-α, D-glucofuranose (a single homogenous spot on TLC) was 16.6 g (92.9%).

NMR (CDCl$_3$): W5.98(d,1H,H$_1$), 4.56(d,1H,H$_2$) 0.87 (t, 3H, CH$_2$, CH$_3$); High resolution MS calculated for C$_{19}$H$_{35}$N,O$_5$ is 357.2515; found 357.2507.

CIMS: 358 (M+1)

EXAMPLE 2

1,2-O-Isopropylidene-6-deoxy-6-aminoundecyl-α, D-glucofuranose

Step 1

A mixture of 1,2:3,5-di-O-isopropylidene-6-tosyl-α, D-glucofuranose (20.7 g, 0.05 mole) as obtained in Step 4 of Example 1 and 1-aminoundecane (21.37 g, 0.125 mole) was heated at 80°-90° C. with stirring, for 2.5 hours. The progess of the reaction was followed by GC and TLC. The reaction mixture was cooled and dissolved in ethyl acetate (250 ml). The organic layer was washed with a saturated solution of sodium bicarbonate (2×50 ml) and brine (2×25 ml) and dried using magnesium sulfate. The crude product obtained after removal of the solvent was purified by flash chromatography (100% ether) to yield the pure compound 1,2:3,5-di-O-isopropylidene-6-deoxy-6-aminoundecyl-α, D-glucofuranose in 92% yield.

Step 2

The product obtained above in step 1 (10 g) was dissolved in 10 ml of tetrahydrofuran and cooled the flask at 0°-5° C. Aqueous perchloric acid (10 ml, 30%) was added dropwise with stirring over a period of 10 minutes. The progess of the reaction was monitored by TLC. When the hydrolysis was complete (1.20 hours) the solution was neutralized with a saturated solution of potassium carbonate to a pH of 9.0 and extracted with ethyl acetate (200 ml). The removal of the solvent gave a crude sample which was purified by crystallization (etherhexane) as a white waxy material, 1,2-O-Isopropylidene-6-deoxy-6-aminoundecyl-α, D-glucofuranose, in 94% yield.

NMR (CDCl$_3$): 5.93(d, 1H,H$_1$), 4.50 (d, 1H,H$_2$), 0.88 (t$_1$ 3H$_1$ CH$_2$ CH$_3$).

CIMS: 374 (M+1); high resolution MS calculated for C$_{20}$H$_{39}$N$_1$ O$_5$ is 373.2828; found: 373.2815.

EXAMPLE 3

1,2-O-Isopropylidene-3-O-(n-heptyl)-6-deoxy-α,D-glucofuranose

Step 1

1,2:5,6-Di-O-Isopropylidene-α,D-glucofuranose (DGF) (10 g; 0.038 moles) and dry powdered sodium hydroxide (5.76g) were blended together and heated at 140° C. under vacuum (1 mm Hg) for a period of 30 minutes with continuous stirring. Sodium salt of DGF so formed was cooled to 120° C. and the vacuum line was disconnected. 1-Bromoheptane (10.32 g; 0.057 moles) was added in the reaction flask and stirred for 1 hour at 120° C. (The progress of the reaction was monitored by TLC). After completion of the reaction, the flask was cooled to ambient temperature and the residue was dissolved in methylene chloride (100 ml)., filtered, washed with $CH_2Cl_2$ (50 ml) and the solvent removed. The crude mixture so obtained was purified by flash chromatomography using Ether:Hexane=70.30. The yield of the pure product, 1,2:5,6-Di-O-isopropylidene-3-O-(n-heptyl)-alpha, D-glucofuranose was 12 g (86.9%).

NMR ($CDCl_3$); S 5.87 (d, 1H, $H_1$), 1.55 (t, 2H, $CH_{2O}$), 0.88 (t, 3H, $CH_2CH_3$).

CIMS: 359 (M+1)

Step 2

1,2:5,6-Di-O-isopropylidene-3-O-(n-heptyl)-α,D-glucofuranose obtained in Step 1 (2.86 g, 7.9 moles) was dissolved in tetrahydrofuran (6 ml). The flask was cooled at 5 C. To this stirred solution was added an ice cold solution of 30% perchloric acid (6 ml) and the mixture stirred for another 38 minutes. (The progress of the reaction was followed by TLC). After the completion of the reaction, a saturated solution of potassium carbonate was added until pH 10 was achieved. The reaction mixture was then filtered through Celite, washed with THF and the solvents were removed under diminished pressure. The product was purified by flash chromatography using 70:30 $Et_2O$:Hexane. The yield of the pure product, 1,2-O-isopropylidene-3-O(n-heptyl)-α,D-glucofuranose was 99%.

NMR ($CDCl_3$): 5.93 (d, 1H), 4.58 (d, 1H), 2.55 (t, 2H), 0.89 (t, 3H).

CIMS: 319 (M+1)

Step 3

To a stirred solution of 1,2-O-isopropylidene-3-O-(n-heptyl)-α,D-glucofuranose (20 g, 0.062 moles) in anhydrous pyridine was added dropwise a solution of p-toluenesulfonyl chloride (11.81 g, 0.062 moles) in anhydrous pyridine (50 ml), at 0-5 C., over a period of 20 minutes. After the complete addition, the reaction mixture was stirred for a period of 4 hours at the same temperature. The progress of the reaction was followed by TLC. The pyridine was then removed under diminished pressure and the residue dissolved in ethyl acetate (250 ml), washed with a saturated solution of sodium bicarbonate (3×50 ml) and brine (2×25 ml). The ethyl acetate layer was dried using anhydrous magnesium sulfate and the solvent removed. The product obtained, 1,2-O-Isopropylidene-3-O-(n-heptyl)-6-tosylalpha,D-glucofuranose, showed a single homogenous spot on TLC (Ether:Hexane=50:50) and was used as such without further purification for the next step. The yield of the pure product was 25.8 g (87%).

NMR ($CDCl_3$): 7.80 (d, 2H, arom.), 7.35 (d, 2H, arom.) 5.86 (d, 1H, $H_1$), 0.89 (t, 3H, $CH_2CH_3$)

CIMS: 475 (M+1)

Step 4

A solution of 1,2-O-isopropylidene-3-O-(n-heptyl)-6-tosyl-α,D-glucofuranose (4.72 g, 0.01 mole) in anhydrous tetrahydrofuran (20 ml) was added dropwise to a stirred suspension of lithium aluminium hydride (0.95 g, 0.025 mole) in dry tetrahydrofuran (20 ml) over a period of 20 minutes, at 0°-5° C. After the complete addition, the reaction mixture was stirred at the same temperature for another 30 minutes. Excess lithium aluminum hydride was decomposed by careful addition of water (2ml) and 5 ml of aqueous sodium hydroxide (15%). The mixture was stirred for another 30 minutes and then filtered through Celite and washed with ethyl acetate. The solvents were removed from the combined filtrate and the residue dissolved in ether (100 ml) and washed with brine (2×20 ml). The ether layer was dried using magnesium sulfate and the solvent removed. The crude product, 1,2-O-isopropylidene-3-O-(n-heptyl)-6-deoxy-α,D-glucofuranose was purified by column chromatography using 10% either in hexane to afford the title compound in 96% (2.9 g) yield.

CIMS: 303 (M+1), 605 (Dimer+1): high resolution MS for $C_{15}H_{27}O_5$(M—$CH_3$ is 287. 1858; found, is 287.1856.

NMR ($CDCl_3$): 5.89 (d, 1H, $H_1$), 4.49 (d, 1H, $H_2$), 0.81 (t, 3H, $CH_2CH_3$)

EXAMPLE 4

1,2-O-Isopropylidene-3-O-(n-heptyl)-6-deoxy-6-aminoheptyl-α, D-glucofuranose A mixture of 1,2-O-isopropylidene-3-O-(n-heptyl)-6-tosyl-α, D-glucofuranose (4.72 g, 0.01 mole) as obtained in Step 3 of Example 3 and 1-aminoheptane (2.87 g, 0.025 mole) was heated at 70°-80° C. for 2.5 hours. The progress of the reaction was followed by TLC and GC. The reaction mixture was then cooled, dissolved in ethyl acetate (150 ml) and washed with a saturated solution of sodium bicarbonate (2×25 ml) and brine (2×25 ml). The organic layer was dried using magnesium sulfate and the solvent removed. The crude product (4.1 g) was purified by column chromatography (100% ether) to afford 3.9 g of pure compound (93.9%) as a light yellow oil which showed a single homogenous spot on TLC.

CIMS: 416 (M+1); high resolution MS for $C_{23}H_{45}N_1O_5$ is 415.3297; found, 415.3301.

NMR ($CDCl_3$): 5.90 (d, 1H, $H_1$), 4.55 (d, 1H, $H_2$), 0.88 ($t_16H$).

EXAMPLE 5

1,2-O-Isopropylidene-5-O-n-heptyl-6-deoxy α, D-glucofuranose

Step 1

A 250 ml 3-necked RB flask was charged with 3.08 g (77 mmol, 2 eq) of a 60% dispersion of sodium hydride in mineral oil, 20 ml of hexane was added and the mixture was stirred for a few minutes. The supernatant liquid was syringed out. The procedure was repeated twice. Then, 50 ml of freshly distilled tetrahydrofuran was added to the flask, and 10 g (38.5 mmol) of 1,2:5,6-di-O-isopropylidene-α,D-glucofuranose, dissolved in 20 ml of THF was slowly added via an addition funnel. The mixture was stirred for approximately 30 minutes until the evolution of hydrogen had ceased, then 9.86 g (57.7 mmol, 1.5 eq) of benzyl bromide was added. The mixture was stirred for 2 hours at room temperature, when GC analysis indicated complete conversion. The excess sodium hydride was quenched with methanol, and the contents of the flask were evaporated to a syrupy mass which was dissolved in 100 ml of ether and washed with water and brine. The ether extract was dried over magnesium sulfate and evaporated to give a syrup, 1,2:5,6-Di-O-isopropylidene-3-O-benzyl-α,D-glucofuranose, yield 13.25 g (98.4%) more than 99% pure by GC.

CIMS: 351 (M+1), 368 (M+18)

Step 2

1,2:5,6-Di-O-isopropylidene-3-O-benzyl-α,D-glucofuranose (20 g, 0.057 mole) was dissolved in 20 ml of tetrahydrofuran and cooled in an ice water bath. Commercial perchloric acid (20 ml, 60%) was diluted with an equal amount of water, and similarly cooled. With vigorous stirring, the aqueous acid was pipetted into the reaction flask, and the progress of the reaction was monitored by thin layer chromatography (ether-hexane 1:1 and ether-hexane 2:1). After 45 minutes, the reaction was complete. The mixture was neutralized with anhydrous potassium carbonate, filtered and the filtrate was concentrated to a syrup which was dissolved in ethyl acetate and washed with brine. Removal of the solvent gave a pale syrup which was purified by flash chromatography (20% ether in hexane, then 50% ether in hexane) to give 15.22 g (86%) of the pure product, 1,2-O-isopropylidene-3-O-benzyl-α,D-glucofuranose, as a pale, viscous syrup.

NMR (CDCl$_3$): 7.35 (5H, m, Ar); 5.935 1H, d, H-1); 4.627 (1H, d, H-2)

CIMS: 328 (M18)

Step 3

1,2-O-isopropylidene-3-O-benzyl-α,D-glucofuranose (15.04 g, 48.5 mmol) was dissolved in 50 ml of anhydrous pyridine and cooled to 5C. An addition funnel was charged with 9.34 g (49 mmol, 1.01 eq) of p-toluene-sulfonyl chloride in 30 ml of anhydrous pyridine, which was slowly added to the substrate over a period 30 minutes (bath temperature 5–10 C.). The mixture was then stirred at room temperature for 18 hours and poured into ice water. The gummy material was extracted with dichloromethane, and washed with water, cold 10% hydrochloric acid, saturated sodium hydrogen carbonate, brine and then dried over magnesium sulfate. Evaporation of the solvent gave 20.82 g (93%) of a glassy material, 1,2-O-isopropylidene-3-O-benzyl-6-O-p-toluenesulfonyl-α,D-glucofuranose which was used without purification for the subsequent reduction.

Step 4

To a stirred slurry of 2.5 g (65.8 mmol, 1.5 eq) of lithium aluminum hydride in 100 ml of anhydrous THF was added, over a period of 25 minutes, 20.74 g (44.7 mmol) of the tosylate dissolved in 100 ml of anhydrous THF. Upon completion of the addition, the mixture was stirred at RT for 45 minutes, whereupon the reaction was complete. The excess lithium aluminum hydride was quenched by cooling and careful addition of ethyl acetate followed by 10% sodium hydroxide solution. The filtrate was evaporated to dryness to give the product which was purified by flash chromatography—15% ethyl acetate in hexane, to yield 10.93 g (83%) of the pure product, 1,2-O-Isopropylidene-3-O-benzyl-6-deoxy-α,D-glucofuranose.

CIMS: 295 (M+1)$_1$ 589 (Dimer+1).

Step 5

Sodium hydride (0.41 g, 1.5 eq) was washed with hexane and slurried in 10 ml of anhydrous N,N-dimethylformamide. A solution of 2.0 g (6.8 mmol) of the 5-hydroxy derivative was dissolved in 5 ml of N,N-dimethylformamide and added to the flask. After 25 minutes of vigorous stirring, 1.5 g (1.23 eq) of 1-bromoheptane was added, and the mixture was stirred at room temperature of 1.5 hours. The excess sodium hydride was quenched with methanol, and the mixture was diluted with water and extracted with ether. Workup of the ether extract gave a quantitative yield of oil, 2.61 g (98%) of 1,2-O-isopropylidene-3-O-benzyl-6-deoxy-5-O-n-heptyl-α,D-glucofuranose.

CIMS: 393 (M+1)

Step 6

The 3-O-benzyl substrate (2.1 g, 5.36 mmol) was dissolved in 15 ml of anhydrous tetrahydrofuran and cooled to −40 C. to −50 C. in a methanol dry-ice bath. Approximately 25 ml of anhydrous ammonia was condensed into the flask, followed by the addition of 0.37 g (16.1 mmol, 3 eq) of sodium metal in three portions. After 20 minutes, the excess sodium metal was quenched by solid ammonium chloride, and the ammonia was allowed to evaporate in a stream of nitrogen. The residue was dissolved in methylene chloride, and filtered. Evaporation of the filtrate and chromatographic purification (5% ethyl acetate in hexane) gave 1.45 g (89.6%) of the pure product, 1,2-O-isopropylidene-6-deoxy-5-O-n-heptyl-α,D-glucofuranose, as an oil.

NMR (CDCl$_3$): 5.96 (d,1H,H$_1$), 4.5 (d$_1$,1H,H$_2$), 0.878(t3HCH$_3$).

CIMS: 303 (M+1); high resolution MS calculated for C$_{16}$H$_{30}$O$_5$ is 302.2093; found, 302.2095.

EXAMPLE 6

1,2-O-Isopropylidene-3-O-3'-(N'-N'-dimethylamino propyl)-5-O-n-heptyl-6-deoxy-α,D-glucofuranose 1,2-O-isopropylidene-6-deoxy-5-O-n-heptyl-α,D-glucofuranose (0.6 g, 2 mmol) as obtained in Example 5 was dissolved in 5 ml of DMF and added to a slurry of 0.16 g (3.95 mmol, 2 eq) of sodium hydride (washed in hexane) in 10 ml of anhydrous N,N-dimethylformamide (DMF). After 20 minutes, 0.36 g (3 mmol, 1.5 eq) of N,N-dimethylaminopropyl chloride was added, and the mixture was stirred for 1.5 hours. The excess sodium hydride was quenched with methanol, and the mixture was partitioned between water and methylene chloride. Workup of the organic extract and chromatographic purification (ether, then ethyl acetate) gave 0.7 g (91%) of the desired product as an oil.

CIMS: 388 (M+1); high resolution MS calculated for C$_{21}$ H$_{41}$ N$_1$O$_5$ is 387.2984; found, 387.2981.

NMR (CDCl$_3$): 5.85 (d, 1H, H$_1$), 4.55 (d, 1H, H$_2$), 2.215(s, 6H, Me$_2$N), 0.883 (t, 3H, CH$_3$)

EXAMPLE 7

1,2-O-Isopropylidene-6-deoxy-6-N-3'-(N',N'-dimethylamino-n-propyl)-α,D-glucofuranose A mixture of 1,2-O-isopropylidene-6-tosyl-α,D-glucofuranose (3 g, 0.013 mol) and 3-dimethylaminopropylamine (4.09 g) was heated in an oil bath at 85C. for 3 hours. The flask was then cooled to an ambient temperature and 100 ml of dichloromethane was added. The organic layer was washed with saturated NaHCO$_3$ (2×10 ml), brine (2×10 ml), dried (magnesium sulfate) and the solvent removed. The crude product so obtained was purified by flash chromatography using (Ether:Methanol=90:10). The yield of the pure product was 3.7 g (91%).

CIMS: 305 (M+1)

EXAMPLE 8

1,2-O-Isopropylidene-3-O-heptyl-6-deoxy-6-S-heptyl-α,D-glucofuranose

Step 1

Lithium bromide (5 g. 0.057 moles) was added to a solution of 1,2-O-isopropylidene-3-O-heptyl-6-tosyl-α,D-glucofuranose (12 g. 0.025 moles) in anhydrous dimethylformamide (100 ml) and the mixture was heated at 70–80C. with stirring for 2.5 hours. Solvent was then distilled off under diminished pressure and the residue dissolved in ethyl acetate (200 ml). The organic layer washed with saturated NaHCO$_3$ solution (2×25 ml), brine (2×10 ml), dried (magnesium sulfate) and the solvent removed. This product 1,2-O-isopropylidene-3-O-heptyl-6-deoxy-6-bromo-α,D-glucofuranose (97%) showed a single homogenous spot on TLC (EtOAc:-Hexane=60:40) and hence used as such for the next step.

CIMS: 382 (M+1)

Step 2

A solution of 1,2-O-isopropylidene-3-O-heptyl-6-deoxy-6-bromo-α,D-glucofuranose (3.81 g., 0.01 mol) in dry THF (10 ml) was added dropwise to a stirred solution of the sodium salt of 1-heptanethiol [formed by reacting 1-heptanethiol (1.32 g, 0.01 mole) with sodium hydride in dry tetrahydrofuran (10 ml)] and the mixture refluxed for one hour under N$_2$. Solvent was then removed and the residue extracted with ethyl acetate, washed with brine (2×10 ml), dried with magnesium sulfate and solvent removed. The product was purified by flash chromatography (EtOAc:Hexane=65:35) to yield a pure compound, 1,2-O-isopropylidene-3-O-heptyl-6-deoxy-6-S-heptyl-α, D-glucofuranose, as a colorless viscous oil in 84% yield.

NMR (CDCl$_3$: 5.90 (d, 1H, H$_1$), 4.55 (d, 1H, H$_2$), 0.88 (t, 6H)

CIMS: 433 (M+1)

EXAMPLE 9

1,2-O-Isopropylidene-5-deoxy-3-O-heptyl-α,D-glucofuranose

Step 1

1,2-O-isopropylidene-3-O-heptyl-α,D-glucofuranose (19.02 g, 0.06 mol) was dissolved in 30 ml of anhydrous N,N-dimethylformamide (DMF) and cooled to 15–20 C. in an ice water bath. Imidazole (4.9 g., 0.072 mol, 1.2 eq.) was added followed by 9.0 g (0.06 mol, 1 eq) of t-butyl dimethylsilyl chloride in three portions. After a total reaction time of 3 hours, the mixture was poured into water and extracted with ether. Workup of the organic phase gave 24.2 g (94%) of the desired compound, 1,2-O-isopropylidene-3-O-heptyl-6-O-t-butyldimethylsi'yl-α,D glucofuranose, of greater than 98% purity.

CIMS: 433 (M+1)

Step 2

1,2-O-isopropylidene-3-O-heptyl-6-O-t-butyldimethylsilyl-α, D-glucofuranose (23.9 g, 0.055 mol), dissolved in 25 ml of DMF, was added to a slurry of 2 g (1.5 eq) of sodium hydride in 55 ml of anhydrous DMF. After evolution of hydrogen had ceased, 10.51 g (0.14 mol) of carbon disulfide was added. The mixture was vigorously stirred for 15 minutes, then 19.64 g (0.14 mol) of iodomethane was added, and the mixture was stirred for an additional 30 minutes and then poured into ice water and extracted with ether. The combined ether extract was washed with water, and brine, dried over magnesium sulfate and evaporated to give the xanthate as a glass. The yield was 26.88 g (93%), consisting of essentially a single component by thin layer chromatography. This compound is 1,2-O-isopropylidene-3-O-heptyl-5-O-[(methylthio)thiocarbonyl-6-O-t-butyldimethysilyl-α, D-glucofuranose.

Step 3

A solution of 21 g (0.04 mol) of the xanthate and 16.2 ml (1.5 eq) of tributyltin hydride in 100 ml of anhydrous toluene was refluxed in a nitrogen atmosphere for 8 hours. The toluene was evaporated, and the residue was dissolved in 100 ml of anhydrous tetrahydrofuran, and 60 ml of a 1.0M solution of tetrabutylammonium fluoride (15.8 g, 1.5 eq) in THF was added. The mixture was refluxed for one hour. Then the mixture was concentrated to a syrup. The residue was dissolved in acetonitrile, and extracted thrice with hexane to remove tribuytltin residues. The acetonitrile phase was evaporated to give 9.84 g (81%) of the crude product, which was purified by chromatography to give 1,2-O-isopropylidene-5-deoxy-3-O-heptyl-α,D-glucofuranose.

NMR: 5.89 (d, H); 4.55 (d, H); 4.33 (m, H); 3.69 (d, H); 0.882 (t, CH$_3$)

CIMS: 303 (M+1)

EXAMPLE 10

1,2-O-Isopropylidene-3-deoxy-5,6-O[3'-di-(N',N'-dimethylamino-n-propyl)]-α,D-glucofuranose Step 1

1,2:5,6-Di-O-isopropylidene-3-deoxy-α,D-glucofuranose (prepared by a well-known procedure described in the literature) (10 g) dissolved in ethanol (10 ml). The flask was cooled to 0–5 C. using ice water. Stirring was started and hydrochloric acid (5M, 10 ml) was added dropwise over a period of 15 minutes. After the complete addition of acid, the reaction mixture was stirred for another 45 minutes at the same temperature. The progress of the reaction was followed by TLC. It was then neutralized with a saturated solution of potassium carbonate to pH 9.0. The reaction mixture was filtered, washed with ethanol and the solvents removed. The residue was dissolved in ethyl acetate (150 ml), washed with brine (2×10 ml), dried over MgSO$_4$ (anhydrous), filtered and the solvent removed. The product was recrystallized from ethanol-water, to afford the compound, 1,2-O-Isopropylidene-3-deoxy-α,D-glucofuranose, in 87% yield, m.p. 80.4–81.4 C.

CIMS 205 (M+1)

Step 2

A mixture of 1,2-O-isopropylidene-3-deoxy-α,D-glucofuranose (2.04 g, 0.01 mole) and dry powdered sodium hydroxide (3 equivalents) was heated at 110–120 C. under diminished pressure (0.1 mm Hg). When all the water formed had been removed (30 minutes), the vacuum line was disconnected and N,N,-dimethylamino-n-propylchloride (3.03 g; 2.5 equivalents) was added. The reaction mixture was then heated at the same temperature for 30 more minutes. The reaction flask was cooled to ambient temperature and 100 ml dichloromethane was added. The salts were filtered off and the solvent was evaporated. The product was purified by flash chromatography using ethyl acetate and ether (50:50) to afford the title compound, 1,2-O-isopropylidene-3- deoxy-5,6-O-[3'-di-(N',N'-dimethylamino-n-propyl)]-α,D-glucofuranose as a light yellow viscous oil in 85% yield.

CIMS 375 (M+1)

EXAMPLE 11

1,2-O-Isocropylidene-3,6-dideoxy-6-N-3'-(N'N'-dimethylamino-n-propyl)-α-D,glucofuranose Step 1

To a stirred solution in dry pyridine (10 ml) of 2.04 g, 0.01 mol, 1,2-O-isopropylidene-3-deoxy-α,D-glucofuranose as prepared in Step 1 of Example 10 was added a solution of p-toluenesulfonyl chloride (1.90 g, 0.01 mol) in dry pyridine (15 ml) at 5–10 C., dropwise over a period of 5 minutes. After the complete addition, the reaction mixture was stirred for another 90 minutes at the same temperature. Pyridine was removed under diminished pressure and the residue was dissolved in ethyl acetate (100 ml), washed with a saturated solution of sodium bicarbonate (2×10 ml), brine (2×10 ml), the organic layer dried and the solvent removed. The crude product, 1-2-O-isopropylidene-3-deoxy-6-tosyl-α,D-glucofuranose, was crystallized from ether to a white crystalline material (2.35 g, 93.5%) of mp 52.0–53.2 C.

NMR (CDCl$_3$): 7.79 (d, 2H, arom), 7.27 (d, 2H, arom), 5.75 (d, 1H, H$_1$), 2.45 (s, 3H CH$_3$) 1, 47., 1.30 (S, 3H each, C(CH$_3$)$_2$)

CIMS 359 (M+1)

Step 2

A mixture of 1,2-O-isopropylidene-3-deoxy-6-tosyl-α,D-glucofuranose (3 g) and N,N-dimethylamino-n-propylamine (3 ml) was heated at 70–80 C. for 2 hours. The progress of the reaction was followed by TLC. After 2 hours, the reaction flask was cooled and 30 ml of dichloromethane was added. The organic layer was washed with brine (2×10 ml), dried and the solvent removed. The product was purified by flash chromatography using 100% ether to afford the title compound, 1,2-O-isopropylidene-3, 6-dideoxy-6-N-3'-(N',N'-dimethylamino-n-propyl)-α,D-glucofuranose. The yield of the pure product was 84%.

EXAMPLE 12

1,2-O-isopropylidene-6-deoxy-6-S-3'-(N',N'-dimethylamino-n-propyl)-α,D-glucofuranose To a well-stirred solution of 1,2:3,5-di-O-isopropylidene-6-deoxy-6-S-3'-(N',N'-dimethylamino-n-propyl)-α,D-glucofuranose (1.6 g) in ethanol (5 ml) was added 5M HCl (4.5 ml) dropwise (5 min.) at 5–10 C. The reaction mixture was stirred for another 20 minutes at the same temperature and then neutralized with aqueous K$_2$CO$_3$ to pH 9.0. It was then extracted with CH$_2$Cl$_2$ (100 ml) and washed with brine (10 ml). The organic layer dried (MgSO$_4$) and solvent removed. The product was purified by flash chromatography using EtOAc:Hexane=70:30 to afford the title compound, as a colorless oil, in 70% yield.

CIMS: 322 (M+1)

NMR (CDCl$_3$): 5.95 (d, 1H, H$_1$), 4.55 (d, 1H, h$_2$), 2.2 (s, 6H, N(CH$_3$)$_2$), 1.32 1.34 (s, 6H, C(CH$_3$)$_2$

EXAMPLE 13

1,2:5,6-Di-O-isocrocylidene-3-deoxy-3-C-ethyl-2'-N-3'-(N'-propylimidazolyl)-α,D-allofuranose Step 1

To a stirred solution of 1,2:5,6-di-O-isopropylidene-3-C-(2'-hydroxyethyl)-α,D-allofuranose [prepared using the procedure as described in the literature—*Journal of Organic Chemistry* 81, 1029, (1969)], (2.88 g, 0.01 mol) in dry pyridine (10 ml) was added dropwise a solution of p-toluenesulfonyl chloride (1.90 g, 0.01 mol) in dry pyridine (10 ml), over a period of 10 minutes at room temperature. After the addition was complete, the mixture was stirred at the same temperature for another hour (followed by TLC). The pyridine was then removed under diminished pressure and cold water (100 ml) was added to the residue. A light yellow solid was formed after scratching with a glass rod. The material, 1,2:5,6-Di-O-isopropylidene-3-deoxy-3-C-(2'- hydroxyethyl)-2'-O-p-tolylsulfonyl-α, D-allofuranose, was filtered and washed with water. It was recrystallized from ethanol, yield 4.4 g (100%), mp 89–90 C.

Step 2

A mixture of the tosyl compound obtained above (2 g) and 1-(3-aminopropyl)imidazole (3 ml) was heated at 70–80C. for 2.5 hours. The progress of the reaction was followed by TLC. The reaction mixture was then cooled to ambient temperature and dissolved in ethyl acetate (100 ml), washed with a saturated solution of NaHCO$_3$ (2×10 ml), brine (2×10 ml), and the organic layer dried with magnesium sulfate and the solvent removed. The residue so obtained was purified using flash chromatography. The yield of the pure product, 1,2:5,6-di-O-isopropylidene-3-deoxy-3-C-ethyl-2'-N-3'-(N'-propylimidazolyl)-alpha,D-allofuranose was 76%.

NMR CDCl$_3$: 5.75 (d, 1H, H$_1$) 4.63 (t, 1H, H$_2$) 1.50, 1.41, 1.34, 1.31, (each s, 3H each, Isopropylidine 4CH$_3$) 7.5, 7.05, 5.95 (all s, 1H each, imidazole protons).

CIMS: 396 (M+1)

The hydrolysis of the title compound was prepared by the same method as cited in Step 1 of Example 10.

EXAMPLE 14

Methyl 2-O-heptyl-D-glucofuranoside

Step 1

1,2-O-isopropylidene-alpha,D-glucofuranose (50 g, 0.23 mol), 250 ml of reagent grade dimethyl sulfoxide and 34 g (0.85 mol, 1.2 eq) of powdered sodium hydroxide were placed in a 1 liter RB flask. The mixture was stirred at room temperature for 30 minutes, then the temperature was raised to 50 C. and 94 ml (1.2 eq) of benzyl chloride was added. The reaction was maintained at 50 C. for 8 hours, then the mixture was filtered. The filtrate was diluted with water and extracted with ether. The organic phase was washed with water, dried (MgSO4) and evaporated to give 93.5 g (84%) of a syrup, 1,2-O-isopropylidene 3,5,6-tri-O-benzyl-α,D-glucofuranose, which was purified by flash chromatography.

CIMS: 491 (M+1)

Step 2

10.24 g, 0.02 mol of the syrup obtained in Step 1 was dissolved in 50 ml of anhydrous methanol containing about 5 g of anhydrous hydrogen chloride, and stirred at room temperature for 1 hour. Thin layer chromatography (2:3 ether-hexane) indicated the conversion of the starting material into two polar components. The hydrogen chloride was neutralized with triethylamine, the mixture was evaporated and the residue was diluted with ether and washed with saturated sodium hydrogen carbonate, brine and dried over MgSO$_4$. Evaporation of the solvent gave 9.27 g (96%) of the anomeric glucofuranosides, methyl 3,5,6-tri-O-benzyl-D- glucofuranosides, which were not separated at this point.

CIMS 465 (M+1)

Step 3

Sodium hydride (1.3 g, 1.5 eq.) was washed with hexane under a nitrogen atmosphere, and then slurried in 20 ml of anhydrous dimethyl sulfoxide. Methyl 3,5,6-tri-O-benzyl-D-glucofuranoside (10 g, 0.222 mol) as obtained in Step 2 was dissolved in 20 ml of dimethylsulfoxide, syringed into the flask, and the mixture was stirred for 15 minutes, followed by the addition of 4.6 g (1.2 eq.) of 1-bromoheptane. After 1.5 hours, the mixture was quenched by the careful addition of methanol, diluted with water, and extracted with ether. Conventional workup of the organic phase gave 11.4 g (94.2%) of the the methyl 3,5,6-tri-O-benzyl-2-O-heptyl-D-glucofuranoside, which was used directly for the final reaction.

Step 4

Methyl 3,5,6-tri-O-benzyl-2-O-heptyl-D-glucofuranoside (10.5 g, 0.019 mol) was dissolved in 25 ml of anhydrous ether and placed in a flask maintained at −40 to −50 C. in an acetone-dry ice bath. Ammonia (100 ml) was condensed into the flask, and 2.05 g (1.6 eq.) of sodium metal was added in small portions, until a deep blue color persisted. The excess sodium metal was quenched by the careful addition of solid ammonium chloride, and the mixture was allowed to warm up to room temperature with nitrogen sparging. The mixture was filtered, the residue was washed with acetone, and the combined filtrate and washings were evaporated to give a syrup which was purified by flash chromatography (70:30 ethyl acetate in hexane, then neat ethyl acetate) to afford 4.96 g (91.3%) of the title compound methyl-2-O-heptyl-D-glucofuranoside, roughly 4:5 as a mixture of alpha and beta anomers. NMR: 4.94 (d, H-1, alpha); 4.88 (s, H-1, beta); 3.41 (S, ome); 3.38 (s, ome) 1.28 (m, 8H, 4 $CH_2$); 0.89 (t, 3H, $CH_3$)

CIMS: 310 (M+18); 602 (Dimer+18)

Pharmacological Activity of the Claimed Compounds

Since the early 1970's it has been known that one of the more important mediators of the inflammatory process is the biosynthesis of leukotrienes and prostaglandins from tissue cells and macrophages at the site of inflammation (Flower et al., 1985). Damage to mammalian cells, either by physical trauma or the combination of an antigen with an antibody, as may be the case with psoriasis, iritates the biosynthesis of these mediators of inflammation, which are, in turn, responsible for the physiological and visible signs of inflammation. In psoriasis, there is an increase in the formation of arachidonic acid in the psoriatic skin that results in mildly increased production of prostaglandins, and a severalfold increase in the concentration of leukotrienes, principally $LTB_4$. $LTB_4$ is the principal biological mediator which is responsible for the promotion of the inflammatory process that exacerbates the disease (Anderson, 1983) and is probably produced by the psoriatic keratinocytes (Kragballe and Herlin, 1983). The tests below demonstrate that the compounds of the present invention have pharmacological activity in reducing $LTB_4$ activity, have an effect in regulating the activity of the infiltrating T-lymphocytes, and have demonstrated antiproliferative activity in skin cells (normal and psoriatic).

Moreover, the activity of the compounds demonstrated in Tables 1, 2 and 3 below indicate that physiologically acceptable doses of these claimed compounds can be used, either topically or systemically, to inhibit T-cell and human fibroblast activity.

An assay was conducted to demonstrate the ability of the compounds of the present invention to modulate T-lymphocyte activity. It is known that the induction and maintenance of most inflammatory diseases are typically due to the unrestricted activity of T-lymphocytes. Therefore, it is advantageous to identify compounds which are modulators of T-lymphocyte activity for eventual use in the regulation of inflammatory diseases, including acquired immune deficiency syndrome, psoriasis, systemic lupus, erythematosus, and rheumatoid arthritis.

A simple method is used to screen compounds for their ability to modulate T-lymphocyte activity which comprises assessing the capacity of the compounds to alter the activation of murine spleen cells in response to T-lymphocyte mitogen activators, such as concanavalin-A (Con-A). The method used to measure the effects of the compounds of the present invention on the blastogenic response of spleen cells to the T-lymphocyte mitogen, (i.e., Con-A), is as follows.

Spleen cells were removed from normal C57Bl/6 mice and homogenized to obtain a single cell suspension. Erythrocytes were lysed by hypotonic shock. Upon determination of the viability and concentration of the remaining lymphoid cells, they were adjusted to a concentration of $4 \times 10^6$/ml. These spleen cells ($2 \times 10^5$ cells per 50ml) were seeded into wells of microtiter plates with the compounds of the present invention having the following dose concentrations:

Group 1: 0 mg/ml
Group 2: 10 mg/ml
Group 3: 25 mg/ml
Group 4: 100 mg/ml
Group 5: 300 mg/ml
Group 6: 750 mg/ml Con-A was also added to these cultures at a final concentration of 4 and 1 mg/ml. These cells were cultured for 3 days at 37° C. in a humidified atmosphere of 5% $CO_2$ in air. For the last 18 hours of culture, 1 mCi$^3$H-thymidine was added to each well. The cells were then precipitated by a multichannel harvester. The amount of $^3$H-thymidine incorporated by the cultured cells were measured in a liquid scintillation counter (Disintegrations per min., DPM). All assays were conducted in triplicate.

The incubation medium used for the blastogenesis assays was RPMI-1640 medium containing 10% fetal bovine serum, 100 mg/ml streptomycin, 100 U/ml penicillin, 0.2M Hepes buffer solution, $5 \times 10^{-5}$M 2-mercaptoethanol and 2 mM glutamine.

The differences in the blastogenic response by splenic T-lymphocytes in the presence of the subject compounds versus the control medium can be seen from data reported in Table 1.

TABLE 1

Effects of Selected Claimed Compounds
On the Con-A Response of Normal Spleen Cells

| Drug | Con-A | Blastogenic response of normal spleen cells to Con-A; % effect |
| --- | --- | --- |

TABLE 1-continued

Effects of Selected Claimed Compounds On the Con-A Response of Normal Spleen Cells

| | | | | | | | |
|---|---|---|---|---|---|---|---|
| none | 4 ug/ml | 97,141 ± 5,802 | | | | | |
| | 1 ug/ml | 72,234 ± 6,650 | | | | | |

| | | Dose of experimental compound added to blastogenesis assay: | | | | | |
|---|---|---|---|---|---|---|---|
| | | 750 ug/ml | 300 ug/ml | 100 ug/ml | 25 ug/ml | 10 ug/ml | 1 ug/ml |
| Ex. 1 | 4 ug/ml | 2,089 ± 35 −98** | 3,097 ± 573 −97** | 4,880 ± 3,619 −95** | 6,201 ± 1,410 −94** | 32,032 ± 1,999 −67** | 116,263 ± 2,521 +20# |
| | 1 ug/ml | 19,688 ± 7,148 −87** | 5,398 ± 4,008 −93** | 10,705 ± 9,501 −85** | 26,920 ± 10,528 −63# | 53,439 ± 9,464 −26* | 93,328 ± 15,583 +29 |
| Ex. 2 | 4 ug/ml | 1,575 ± 480 −98** | 2,787 ± 413 −97** | 2,618 ± 444 −97** | 1,635 ± 635 −98** | 4,293 ± 3,517 −96** | 18,607 ± 8,159 −81** |
| | 1 ug/ml | 2,020 ± 651 −97** | 2,934 ± 299 −96** | 2,967 ± 964 −96** | 3,312 ± 1,541 −95** | 5,014 ± 89 −93** | 13,581 ± 4,804 −81** |
| Ex. 4 | 4 ug/ml | 3,128 ± 99 −97** | 4,919 ± 645 −95** | 7,102 ± 6,851 −93** | 13,114 ± 8,696 −86** | 7,789 ± 7,636 −92** | 41,151 ± 9,885 −58# |
| | 1 ug/ml | 3,762 ± 1,201 −95** | 9,102 ± 6,857 −87** | 5,241 ± 2,071 −93** | 3,575 ± 827 −95** | 3,406 ± 422 −95** | 22,026 ± 9,838 −70# |
| Ex. 5 | 4 ug/ml | 4,494 ± 2,952 −95** | 5,932 ± 2,770 −94** | 2,299 ± 490 −98** | 62,068 ± 3,736 −36** | 92,190 ± 13,256 −5 | 116,377 ± 12,433 +20 |
| | 1 ug/ml | 9,487 ± 7,951 −87** | 8,698 ± 786 −88** | 8,553 ± 9,274 −88** | 63,177 ± 13,102 −13 | 79,822 ± 15,967 +11 | 91,612 ± 15,530 +27 |
| Ex. 6 | 4 ug/ml | 2,933 ± 1,383 −97** | 3,756 ± 923 −96** | 6,741 ± 4,224 −93** | 6,187 ± 6,859 −94** | 4,693 ± 1,930 −95** | 75,689 ± 8,498 −22* |
| | 1 ug/ml | 3,709 ± 281 −95** | 3,693 ± 340 −95** | 6,597 ± 2,887 −91** | 5,399 ± 3,253 −93** | 12,670 ± 6,997 −82** | 86,406 ± 16,348 +20 |
| Ethanol blank | 4 ug/ml | 77,634 ± 8,964 −20 | 87,766 ± 23,543 −10 | 114,938 ± 18,478 +18 | 109,814 ± 6,244 +13 | 89,715 ± 19,994 −8 | 106,607 ± 7,499 +12 |
| | 1 ug/ml | 96,724 ± 15,077 +34 | 65,442 ± 2,767 −9 | 83,301 ± 9,990 +15 | 84,895 ± 12,493 +18 | 73,425 ± 10,535 +2 | 87,683 ± 14,614 +21 |
| DMSO blank | 4 ug/ml | 2,697 ± 522 −97** | 24,433 ± 5,097 −75** | 84,374 ± 14,085 −13 | 126,709 ± 36,243 +30 | 119,609 ± 3,597 +23# | 159,437 ± 19,004 +64# |
| | 1 ug/ml | 3,249 ± 126 −96** | 9,348 ± 1,709 −87** | 60,938 ± 22,253 −16 | 109,786 ± 21,954 +52* | 84,690 ± 4,752 +17 | 97,030 ± 28,034 +34 |

<sup>a</sup>Experimental compounds were first suspended in DMSO or ethanol, then diluted into medium and added at various concentrations to normal spleen cells and either 4 or 1 ug/ml Con-A. Control cultures contained comparable concentrations of DMSO or ethanol. The effect of these compounds on the blastogenic response of the spleen cells was assessed by pulsing the cells with $^3$H-thymidine after 48 hours of culture and harvesting the spleen cells 18 hours thereafter. Data are expressed as cpm of triplicates ± SD.
<sup>b</sup>The effect of experimental compounds on the blastogenic response of normal splenic T-lymphocytes is expressed as percent change from the response of spleen cells cultured in the absence of experimental compounds. Significance of the effect of experimental compounds: *$P < 0.05$; #$P < 0.01$; **$P < 0.001$.

The results of Table 1 indicate that the compounds of the present invention produced dose-dependent, significant inhibitory effects upon the ability of normal, splenically-derived, mouse T-cells to proliferate in response to mitogenic stimulation. There were marked by fewer T-cells in treated cultures at the end of the assay in comparison to the untreated control cultures.

The compounds of this invention are approximately 10–1000 times more potent than THERAFECTIN ® since significant inhibition was observed at 1, 10 and 100 mg/ml, as opposed to the usual 1,000 ug/ml for THERAFECTIN ®. Since the T-cell is the primary immuno-regulatory cell of the body, this effect suggests that compounds of the present invention have anti-inflammatory and anti-proliferative utility, from a therapeutic standpoint, in the treatment of a variety of autoimmune diseases.

A compound that inhibits skin cell proliferation, has the potential to be utilized as a dermatological drug used to treat various skin disorders such as psoriasis. Also, an anti-proliferative effect may well be observed with other tissues, such as those that line blood vessels, or joints, the uncontrolled proliferation of which produce disease, thereby broadening the scope of potential applications.

A second assay was conducted to demonstrate inhibitory activity of the compounds of the present invention to the in vitro proliferation of human skin cells in tissue culture. The human skin cell fibroblast line, BUD-8, was originally derived from the normal skin of a 56 year old white female and can now be obtained from the American Type Culture Collection.

The number of BUD-8 cells was expanded for use by culture in 25 cm$^2$ flasks at 37° C. in an atmosphere of 5% CO$_2$ in air. At approximately 4–5 five day intervals, or when confluence was reached, the cells were passaged. This was accomplished by detaching the cells with a Teflon scraper, washing and reseeding the cells at a lower density into fresh tissue culture flasks.

The effect of these compound on the proliferative capacity of human BUD-8 skin fibroblasts was measured with the use of a $^3$H-thymidine incorporation assay using culture conditions which were similar to those used for the Con-A blastogenesis assay, described previously. Cultured skin cells were detached from the surface of tissue culture flasks mechanically with a Teflon scraper. The cells were washed, resuspended in incubation medium and the viabilities were determined. These cells were then plated in triplicate at a density of 2 × 10$^3$ cells/0.1 ml/microtiter well for the proliferation assays. After 3 days of culture, luCi $^3$H-thymidine was added in a 50 ul volume to each culture well of the microtiter plates. Eighteen hours later, each of the BUD-8 cultures was examined morphologically for evidence of compound-induced toxicity such as cell rounding or granularity. The thymidine-pulsed cells were then precipitated and the amount of $^3$H-thymidine incorporation was counted in a liquid scintillation counter.

The concentrations of the compounds which were used in this assay were: 1, 10, 25, 100, 300 and 750 mg/ml.

The difference between the inhibitive effect on skin cells cultured in the presence of the compounds of the present invention versus the control medium alone can be seen from the results set forth in Table 2.

BUD-8 skin cell culture supernatants were used directly in the radioimmunoassay. The tubes were refrigerated

TABLE 2
Effect of Selected Claimed Compounds On the Proliferation of BUD-8 Skin Cell Fibroblasts

| Drug | $^3$H-Thymidine uptake by BUD-8 skin cells; % effect | | | | | |
|---|---|---|---|---|---|---|
| none | 6,164 ± 469 | | | | | |
| | Dose of experimental compound added to BUD-8 cells: | | | | | |
| | 750 ug/ml | 300 ug/ml | 100 ug/ml | 25 ug/ml | 10 ug/ml | 1 ug/ml |
| Ex. 2 | 911 ± 863 −85c | 595 ± 110 −90c | 649 ± 114 −89c | 1,430 ± 1,176 −77# | 3,363 ± 227 −46 | 6,069 ± 636 −1 |
| Ex. 3 | 3,496 ± 1,084 −43*c | 2,067 ± 302 −66**c | 4,288 ± 723 −30* | 4,978 ± 632 −19 | 3,139 ± 232 −49** | 2,589 ± 202 −58** |
| Ethanol | 4,800 ± 950 −22 | 5,064 ± 1,264 −18 | 5,311 ± 367 −14 | 4,877 ± 1,119 −21 | 6,748 ± 481 +9 | 5,947 ± 1,484 −4 |
| DMSO | 1,302 ± 296 −79c | 1,479 ± 462 −76 | 6,742 ± 617 +9 | 7,410 ± 902 +20 | 6,742 ± 718 +9 | 6,397 ± 26 +4 |

<sup>a</sup>Experimental compounds were first suspended in DMSO or ethanol, then diluted into medium and added at various concentrations to human BUD-8 skin cell fibroblasts. Control cultures contained comparable concentrations of DMSO or ethanol. The effect of these compounds on the proliferation of the BUD-8 skin cells was assessed by pulsing the cells with $^3$H-thymidine after 72 hours of culture and harvesting the BUD-8 cells 18 hours thereafter.
Data are expressed as cpm of triplicates ± SD.
<sup>b</sup>The effect of experimental compounds on the proliferation of BUD-8 cells is expressed as percent change from the amount of $^3$H-thymidine incorporated in the absense of experimental compounds. Significance of the effect of experimental compounds: *P < 0.05; #P < 0.01, **P < 0.001.
<sup>c</sup>Evidence of toxicity of compound on BUD-8 cells on the basis of either cell rounding or granularity.

As can be seen from Table 2, the compound of Examples 2 & 3 produced an anti-proliferative effect that was statistically significant at a dose that is biologically attainable.

It was also observed that the compound of Example 2 produced an effect upon the secretion of leukotriene B$_4$ (LTB$_4$) into the culture medium of the BUD-8 cells. LTB$_4$ is considered to be one of the substances that contributes to the inflammatory component observed in psoriasis and other skin disorders.

Levels of LTB$_4$ in aliquots of BUD-8 skin cell cultures supernatants were quantified by radioimmunoassay. The cells were first plated in triplicate at a density of 1×10$^4$ cells/0.1 ml/microtiter well for the assay to quantitate LTB$_4$. To these cells was added 0.1 ml incubation medium containing compound 80182, or nordihydroguaiaretic acid (NDGA) to inhibit leukotriene production.

After 18 hours of culture, samples of the BUD-8 skin cell supernatants were collected from one set of microtiter plates and frozen until assayed for LTB$_4$ content using a radioimmunoassay. Into a polypropylene tube were mixed 0.1 ml anti-LTB$_4$, 0.1 ml$^3$H-LTB$_4$ and 0.1 ml LTB$_4$ standard or LTB$_4$ containing sample. The BUD-8 skin cell culture supernatants were used directly in the radioimmunoassay. The tubes were refrigerated overnight. A charcoal solution (0.5 ml of 0.5% charcoal Norit A) was added and each tube was centrifuged. The radio activity in the supernatant was then counted in a liquid scintillation counter.

The results of the LTB$_4$ assay are shown below in Table-3.

TABLE 3
Effects of Selected Claimed Compounds on the Secretion of LTB$_4$ by BUD-8 Skin Cell Fibroblasts<sup>a</sup>

| Drug | pg LTB$_4$/100 ul supernatant (LTB$_4$ secreted/10$^5$ BUD-8 cells); % Effect | | | | | |
|---|---|---|---|---|---|---|
| None | 38.8 ± 1.6 (749) | | | | | |
| | Dose of experimental compound added to BUD-8 skin cells: | | | | | |
| | 750 ug/ml | 300 ug/ml | 100 ug/ml | 25 ug/ml | 10 ug/ml | 1 ug/ml |
| Ex. 2 | 22.4 ± 4.2 (422) −42#c | 15.3 ± 1.1 (281) −60**c | 30.1 ± 3.9 (575) −22*c | 16.4 ± 2.0 (303) −58** | 24.6 ± 5.3 (485) −37* | 44.4 ± 3.8 (862) +15 |
| Ethanol | 33.7 ± 0.0 (647) −13# | 42.0 ± 2.6 (814) +8 | 42.4 ± 8.1 (822) +9 | 38.5 ± 4.0 (744) −1 | 37.8 ± 0.7 (730) −2 | 41.0 ± 0.7 (794) 6+ |
| DMSO | 16.6 ± 2.5 (308) −57**c | 27.7 ± 3.5 (527) −29# | 35.6 ± 4.9 (685) −8 | 31.8 ± 1.3 (611) −18# | 33.3 ± 1.6 (640) −14* | 36.4 ± 2.6 (702) −6 |

<sup>a</sup>Experimental compounds were first suspended in DMSO or ethanol, then diluted into medium and added at various concentrations to human BUD-8 skin cell fibroblasts. The effect of these compounds on BUD-8 cell secretion of LTB$_4$ was assessed by radioimmunoassay. All values are the results of triplicate determinations. Data are expressed as pg LTB$_4$ in 100 ul supernatant ± SD. In parentheses is the calculated pg LTB$_4$ secreted per 10$^5$ cells.
<sup>b</sup>The effect of experimental compounds on the amount of LTB$_4$ in the supernatants of BUD-8 skin cells is expressed as percent change from the amount of LTB$_4$ of cells cultured in the absence of experimental compounds. Significance of the effect of experimental compounds: *P < 0.05; #P < 0.01; **P < 0.001.
<sup>c</sup>Evidence of toxicity of compound on BUD-8 cells on the basis of either cell rounding or granularity.

The NDGA control was not run concurrently with this particular assay but generally produces a level of inhibition in LTB$_4$ levels averaging 46% of control.

The data indicate that, at the same concentrations that inhibit the proliferation of the skin cells without cytotoxicity, LTB$_4$ levels are also decreased in a dose-dependent and significant manner.

In summary, the compounds described in this invention display inhibitory effects upon T-cells, on human skin cell fibroblasts and on their ability to secrete LTB$_4$ at doses that are physiologically attainable either systemically or topically.

What is claimed is:

1. A monosaccharide compound of the formula I

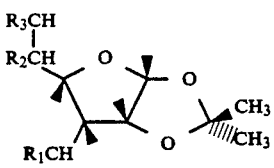

wherein $R_1$ is a member selected from the group consisting of hydrogen, an alkoxyl radical containing from 4 to 11 carbon atoms, a hydroxyl residue, an aralkyl radical containing at least 7 carbon atoms, and a radical of the formula

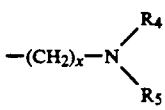

in which x is a whole number up to 7 and $R_4$ and $R_5$ are each H, OH, or an alkoxy radical of up to 7 carbon atoms;

$R_2$ is a member selected from the group consisting of hydrogen, an alkoxy radical containing from 4 to 7 carbon atoms, a methylthio carbonyl, and a radical of the formula

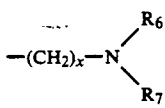

in which x is a whole number up to 7 and $R_6$ and $R_7$ are each H,OH, or an alkoxyl radical of up to 7 carbon atoms;

$R_1$ and $R_2$ together can form an isopropylidene radical;

$R_3$ is a member selected from the group consisting of hydrogen, a halogen, an alkylene radical, an aralkyl radical containing at least 7 carbon atoms, a radical of the formula

in which $R_8$ is hydrogen and $R_9$ is an alkyl radical containing up to eleven carbon atoms and a radical of the formula

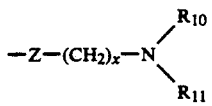

in which Z is thio or amino, x is a whole number up to 7 and $R_{10}$ and $R_{11}$ are each H, OH or an alkoxyl radical of up to 7 carbon atoms; and $R_2$ and $R_3$ together can form an isopropylidene radical.

2. A monosaccharide compound according to claim 1, wherein the monosaccharide is 1,2:3,5-Di-O-isopropylidene-6-deoxy-6-amino-heptyl-α,D-glucofuranose.

3. A monosaccharide compound according to claim 1, wherein the monosaccharide is 1,2-O-isopropylidene-6-deoxy-6-aminoundecyl-α,D-glucofuranose.

4. A monosaccharide compound according to claim 1, wherein the monosaccharide is 1,2-O-isopropylidene-3-O-(n-heptyl)-6-deoxy-α,D-glucofuranose.

5. A monosaccharide compound according to claim 1, wherein the monosaccharide is 1,2-O-isopropylidene-3-O-(n-heptyl)-6-deoxy-6-aminoheptyl-α,D-glucofuranose.

6. A monosaccharide compound according to claim 1, wherein the monosaccharide is 1,2-O-isopropylidene-5-O-n-heptyl-6-deoxy-α,D-glucofuranose.

7. A monosaccharide compound according to claim 1, wherein the monosaccharide is 1,2-O-isopropylidene-3-O-3'-(N'-N'-dimethylaminopropyl)-5-O-n-heptyl-6-deoxy-α,D-glucofuranose.

8. A monosaccharide compound according to claim 1, wherein the monosaccharide is 1,2-O-isopropylidene-6-deoxy-6-N-3-(N',N'-dimethylamino-n-propyl)-α,D-glucofuranose.

9. A monosaccharide compound according to claim 1, wherein the monosaccharide is 1,2-O-isopropylidene-3-O-heptyl-6-deoxy-6-S-heptyl-α,D-glucofuranose.

10. A monosaccharide compound according to claim 1, wherein the monosaccharide is 1,2-O-isopropylidene-5-deoxy-3-O-(heptyl) α,D-glucofuranose.

11. A monosaccharide compound according to claim 1, wherein the monosaccharide is 1,2-O-isopropylidene-3-deoxy-5,6-3'-di(N',N'-dimethylamino-n-propyl)]-α,D-glucofuranose.

12. A monosaccharide compound according to claim 1, wherein the monosaccharide is 1,2-O-isopropylidene-3,6-dideoxy-6-N-3'-(N',N'-dimethylamino-n-propyl)-α,D-glucofuranose.

13. A monosaccharide compound according to claim 1, wherein the monosaccharide is 1,2-O-isopropylidene-6-deoxy-6-S-3'-(N',N'-dimethylamino-n-propyl)-α,D-glucofuranose.

14. A monosaccharide compound according to claim 1, wherein the monosaccharide is 1,2-O-6-Di-O-isopropylidene-3-deoxy-3-C-ethyl-2'-N-3'-(N'-propylimidazolyl)-α,D-allofuranose.

15. A monosaccharide compound wherein the monosaccharide is methyl 2-O-heptyl-D-glucofuranoside.

16. A pharmaceutical composition for the treatment of inflammatory and/or autoimmune disorders which comprises an effective amount of a compound of claim 1 or a physiologically acceptable acid-addition salt thereof with a pharmaceutically acceptable carrier.

17. A pharmaceutical composition for the treatment of inflammatory and/or autoimmune disorders which comprises an effective amount of the compound of claim 2 or a physiologically acceptable acid-addition salt thereof with a pharmaceutically acceptable carrier.

18. A pharmaceutical composition for the treatment of inflammatory and/or autoimmune disorders which comprises an effective amount of the compound of claim 3 or a physiologically acceptable acid-addition salt thereof with a pharmaceutically acceptable carrier.

19. A pharmaceutical composition for the treatment of inflammatory and/or autoimmune disorders which comprises an effective amount of the compound of claim 4 or a physiologically acceptable acid-addition salt thereof with a pharmaceutically acceptable carrier.

20. A pharmaceutical composition for the treatment of inflammatory and/or autoimmune disorders which comprises an effective amount of the compound of claim 5 or a physiologically acceptable acid-addition salt thereof with a pharmaceutically acceptable carrier.

21. A pharmaceutical composition for the treatment of inflammatory and/or autoimmune disorders which comprises an effective amount of the compound of claim 6 or a physiologically acceptable acid-addition salt thereof with a pharmaceutically acceptable carrier.

22. A pharmaceutical composition for the treatment of inflammatory and/or autoimmune disorders which comprises an effective amount of the compound of claim 7 or a physiologically acceptable acid-addition salt thereof with a pharmaceutically acceptable carrier.

23. A pharmaceutical composition for the treatment of inflammatory and/or autoimmune disorders which comprises an effective amount of the compound of claim 8 or a physiologically acceptable acid-addition salt thereof with a pharmaceutically acceptable carrier.

24. A pharmaceutical composition for the treatment of inflammatory and/or autoimmune disorders which comprises an effective amount of the compound of claim 9 or a physiologically acceptable acid-addition salt thereof with a pharmaceutically acceptable carrier.

25. A pharmaceutical composition for the treatment of inflammatory and/or autoimmune disorders which comprises an effective amount of the compound of claim 10 or a physiologically acceptable acid-addition salt thereof with a pharmaceutically acceptable carrier.

26. A pharmaceutical composition for the treatment of inflammatory and/or autoimmune disorders which comprises an effective amount of the compound of claim 11 or a physiologically acceptable acid-addition salt thereof with a pharmaceutically acceptable carrier.

27. A pharmaceutical composition for the treatment of inflammatory and/or autoimmune disorders which comprises an effective amount of the compound of claim 12 or a physiologically acceptable acid-addition salt thereof with a pharmaceutically acceptable carrier.

28. A pharmaceutical composition for the treatment of inflammatory and/or autoimmune disorders which comprises an effective amount of the compound of claim 13 or a physiologically acceptable acid-addition salt thereof with a pharmaceutically acceptable carrier.

29. A pharmaceutical composition for the treatment of inflammatory and/or autoimmune disorders which comprises an effective amount of the compound of claim 14 or a physiologically acceptable acid-addition salt thereof with a pharmaceutically acceptable carrier.

30. A pharmaceutical composition for the treatment of inflammatory and/or autoimmune disorders which comprises an effective amount of the compound of claim 15 or a physiologically acceptable acid-addition salt thereof with a pharmaceutically acceptable carrier.

31. A pharmaceutical composition of claim 16 for the treatment of psoriasis.

32. A pharmaceutical composition of claim 17 for the treatment of psoriasis.

33. A pharmaceutical composition of claim 18 for the treatment of psoriasis.

34. A pharmaceutical composition of claim 19 for the treatment of psoriasis.

35. A pharmaceutical composition of claim 20 for the treatment of psoriasis.

36. A pharmaceutical composition of claim 21 for the treatment of psoriasis.

37. A pharmaceutical composition of claim 22 for the treatment of psoriasis.

38. A pharmaceutical composition of claim 23 for the treatment of psoriasis.

39. A pharmaceutical composition of claim 24 for the treatment of psoriasis.

40. A pharmaceutical composition of claim 25 for the treatment of psoriasis.

41. A pharmaceutical composition of claim 26 for the treatment of psoriasis.

42. A pharmaceutical composition of claim 27 for the treatment of psoriasis.

43. A pharmaceutical composition of claim 28 for the treatment of psoriasis.

44. A pharmaceutical composition of claim 29 for the treatment of psoriasis.

45. A pharmaceutical composition of claim 30 for the treatment of psoriasis.

46. A method for treating an animal or human suffering from inflammatory and/or autoimmune disorders which comprises administering thereto an effective amount of a compound of claim 1 or a physiologically acceptable acid-addition salt thereof.

47. A method for treating an animal or human suffering from inflammatory and/or autoimmune disorders which comprises administering thereto an effective amount of the compound of claim 2 or a physiologically acceptable acid-addition salt thereof.

48. A method for treating an animal or human suffering from inflammatory and/or autoimmune disorders which comprises administering thereto an effective amount of the compound of claim 3 or a physiologically acceptable acid-addition salt thereof.

49. A method for treating an animal or human suffering from inflammatory and/or autoimmune disorders which comprises administering thereto an effective amount of the compound of claim 4 or a physiologically acceptable acid-addition salt thereof.

50. A method for treating an animal or human suffering from inflammatory and/or autoimmune disorders which comprises administering thereto an effective amount of the compound of claim 5 or a physiologically acceptable acid-addition salt thereof.

51. A method for treating an animal or human suffering from inflammatory and/or autoimmune disorders which comprises administering thereto an effective amount of the compound of claim 6 or a physiologically acceptable acid-addition salt thereof.

52. A method for treating an animal or human suffering from inflammatory and/or autoimmune disorders which comprises administering thereto an effective amount of the compound of claim 7 or a physiologically acceptable acid-addition salt thereof.

53. A method for treating an animal or human suffering from inflammatory and/or autoimmune disorders which comprises administering thereto an effective amount of the compound of claim 8 or a physiologically acceptable acid-addition salt thereof.

54. A method for treating an animal or human suffering from inflammatory and/or autoimmune disorders which comprises administering thereto an effective amount of the compound of claim 9 or a physiologically acceptable acid-addition salt thereof.

55. A method for treating an animal or human suffering from inflammatory and/or autoimmune disorders which comprises administering thereto an effective amount of the compound of claim 10 or a physiologically acceptable acid-addition salt thereof.

56. A method for treating an animal or human suffering from inflammatory and/or autoimmune disorders which comprises administering thereto an effective amount of the compound of claim 11 or a physiologically acceptable acid-addition salt thereof.

57. A method for treating an animal or human suffering from inflammatory and/or autoimmune disorders which comprises administering thereto an effective amount of the compound of claim 12 or a physiologically acceptable acid-addition salt thereof.

58. A method for treating an animal or human suffering from inflammatory and/or autoimmune disorders which comprises administering thereto an effective amount of the compound of claim 13 or a physiologically acceptable acid-addition salt thereof.

59. A method for treating an animal or human suffering from inflammatory and/or autoimmune disorders which comprises administering thereto an effective amount of the compound of claim 14 or a physiologically acceptable acid-addition salt thereof.

60. A method for treating an animal or human suffering from inflammatory and/or autoimmune disorders which comprises administering thereto an effective amount of the compound of claim 15 or a physiologically acceptable acid-addition salt thereof.

61. The method of claim 46, which further comprises administering the compound orally.

62. The method of claim 47, which further comprises administering the compound orally.

63. The method of claim 48, which further comprises administering the compound orally.

64. The method of claim 49, which further comprises administering the compound orally.

65. The method of claim 50, which further comprises administering the compound orally.

66. The method of claim 51, which further comprises administering the compound orally.

67. The method of claim 52, which further comprises administering the compound orally.

68. The method of claim 53, which further comprises administering the compound orally.

69. The method of claim 54, which further comprises adminstering the compound orally.

70. The method of claim 55, which further comprises adminstering the compound orally.

71. The method of claim 56, which further comprises adminstering the compound orally.

72. The method of claim 57, which further comprises administering the compound orally.

73. The method of claim 58, which further comprises administering the compound orally.

74. The method of claim 59, which further comprises administering the compound orally.

75. A method of claim 46 for treating an animal or human suffering from psoriasis.

76. A method of claim 47 for treating an animal or human suffering from psoriasis.

77. A method of claim 48 for treating an animal or human suffering from psoriasis.

78. A method of claim 49 for treating an animal or human suffering from psoriasis.

79. A method of claim 50 for treating an animal or human suffering from psoriasis.

80. A method of claim 51 for treating an animal or human suffering from psoriasis.

81. A method of claim 52 for treating an animal or human suffering from psoriasis.

82. A method of claim 53 for treating an animal or human suffering from psoriasis.

83. A method of claim 54 for treating an animal or human suffering from psoriasis.

84. A method of claim 55 for treating an animal or human suffering from psoriasis.

85. A method of claim 56 for treating an animal or human suffering from psoriasis.

86. A method of claim 57 for treating an animal or human suffering from psoriasis.

87. A method of claim 58 for treating an animal or human suffering from psoriasis.

88. A method of claim 59 for treating an animal or human suffering from psoriasis.

89. A method of claim 60 for treating an animal or human suffering from psoriasis.

90. The method of claim 75, which further comprises adminstering the compound orally.

91. The method of claim 76, which further comprises instering the compound orally.

92. The method of claim 77, which further comprises adminstering the compound orally.

93. The method of claim 78, which further comprises administering the compound orally.

94. The method of claim 79, which further comprises administering the compound orally.

95. The method of claim 80, which further comprises administering the compound orally.

96. The method of claim 81, which further comprises administering the compound orally.

97. The method of claim 82, which further comprises administering the compound orally.

98. The method of claim 83, which further comprises administering the compound orally.

99. The method of claim 84, which further comprises administering the compound orally.

100. The method of claim 85, which further comprises administering the compound orally.

101. The method of claim 86, which further comprises administering the compound orally.

102. The method of claim 87, which further comprises administering the compound orally.

103. The method of claim 88, which further comprises administering the compound orally.

104. The method of claim 89, which further comprises administering the compound orally.

* * * * *

UNITED STATES PATENT AND TRADEMARK OFFICE
CERTIFICATE OF CORRECTION

PATENT NO. : 5,010,058
DATED : April 23, 1991
INVENTOR(S) : RONSEN et al.

It is certified that error appears in the above-identified patent and that said Letters Patent is hereby corrected as shown below:

Title page, after "[73] Assignee:" delete "501".

Column 5, formula IV, should read as follows:

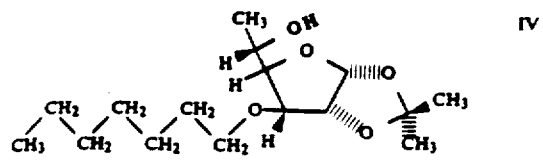

Column 5, formula V, should read as follows:

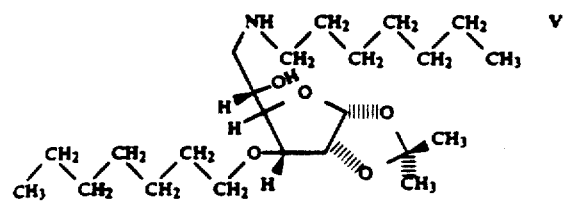

UNITED STATES PATENT AND TRADEMARK OFFICE
CERTIFICATE OF CORRECTION

PATENT NO. : 5,010,058

DATED : April 23, 1991

INVENTOR(S) : RONSEN et al.

It is certified that error appears in the above-identified patent and that said Letters Patent is hereby corrected as shown below:

Column 6, line 11, "6-deoxy 6-S" should read --6-deoxy-6-S--; column 6, formula IX, the portion of the formula reading "$CH_2(CH_2)_3-CH_3$" should read --$CH_2(CH_2)_5-CH_3$--; and column 6, formula XII, should read as follows:

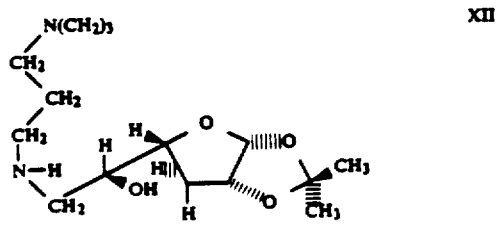

Column 7, formula XIV, the methyl group "$CH_3$" appearing at line 19 should be connected to the remainder of the formula by a line as follows:

UNITED STATES PATENT AND TRADEMARK OFFICE
CERTIFICATE OF CORRECTION

PATENT NO. : 5,010,058

DATED : April 23, 1991

INVENTOR(S) : RONSEN et al.

It is certified that error appears in the above-identified patent and that said Letters Patent is hereby corrected as shown below:

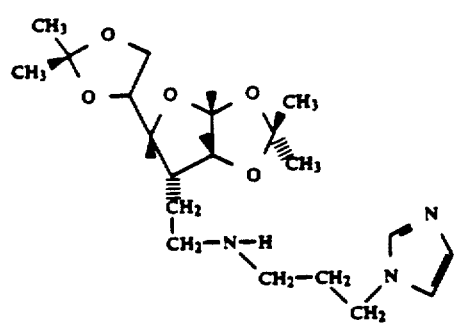

Column 10, line 6, "etherhexane" should read --ether-hexane--; and column 10, line 62, "etherhexane" should read --ether-hexane--.

Column 17, line 6, the portion of the title which is "Isocropylidene" should read --Isopropylidene--; and column 17, line 63, the portion of the title which is "isocrocylidene" should read --Isopropylidene--.

UNITED STATES PATENT AND TRADEMARK OFFICE
CERTIFICATE OF CORRECTION

PATENT NO. : 5,010,058

DATED : April 23, 1991

INVENTOR(S) : RONSEN et al.

It is certified that error appears in the above-identified patent and that said Letters Patent is hereby corrected as shown below:

In claim 14, line 2, "1,2-O-6-Di-O-iso-" should read -- 1,2:5,6-Di-O-iso---.

Signed and Sealed this

Third Day of November, 1992

Attest:

DOUGLAS B. COMER

*Attesting Officer*     *Acting Commissioner of Patents and Trademarks*